United States Patent [19]

Kuroyanagi et al.

[11] Patent Number: 4,642,118
[45] Date of Patent: Feb. 10, 1987

[54] MAN-MADE SKIN COMPOSED OF TWO LAYERS: COLLAGEN AND A POLY-ALPHA-AMINO ACID

[75] Inventors: Yoshimitsu Kuroyanagi, Hachiogi; Teruo Miyata; Manabu Seno, both of Tokyo, all of Japan

[73] Assignee: Koken Co., Ltd., Tokyo, Japan

[21] Appl. No.: 741,835

[22] Filed: Jun. 6, 1985

[30] Foreign Application Priority Data

Nov. 6, 1984 [JP] Japan .................. 59-118276

[51] Int. Cl.$^4$ .............................................. A61F 2/10
[52] U.S. Cl. ...................................................... 623/15
[58] Field of Search ..................... 623/15; 128/DIG. 8

[56] References Cited

U.S. PATENT DOCUMENTS

| | | | |
|---|---|---|---|
| 4,377,010 | 3/1983 | Fydelor | 623/15 |
| 4,394,370 | 7/1983 | Jefferies | 623/15 |
| 4,448,718 | 5/1984 | Yannas | 128/DIG. 8 |

Primary Examiner—Gregory E. McNeill
Attorney, Agent, or Firm—Sherman and Shalloway

[57] ABSTRACT

This invention concerns a double-layered man-made skin which is prepared by laminating a collagen sponge sheet and a poly-α-amino acid membrane that has a good affinity with tissue cells and an appropriate permeability for moisture. When the man-made skin is applied on burns, cuts or wounds, the fibroblasts proliferate in the collagen sponge sheet forming a three-dimensional structure, while the epidermal cells proliferate in the region between the poly-α-amino acid membrane and a collagen sponge sheet. The poly-α-amino acid membrane plays a role in protecting affected part and in providing an optimum condition for the proliferation of fibroblasts and epidermal cells, and then it falls off as the epidermis completely regenerates. On the other hand, the collagen sponge sheet assimilates in the living tissue after having played a general role of the dermis.

9 Claims, 2 Drawing Figures

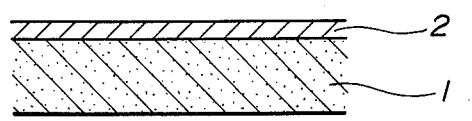
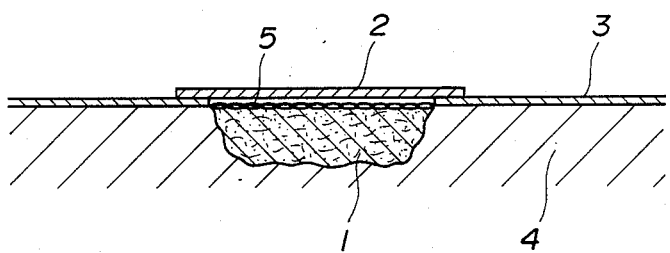

MAN-MADE SKIN COMPOSED OF TWO LAYERS: COLLAGEN AND A POLY-ALPHA-AMINO ACID

FIELD OF THE INVENTION

This invention relates to a man-made skin intended for a use in healing burns, cuts or wounds.

DESCRIPTION OF THE PRIOR ART

Collagen has so far been used for a man-made skin because of being effective in helping the growth of tissue cells. For example, a Japanese patent publication of which laid-open number is No. sho 50-141190 discloses the employment of a collagen-based non-woven fabric for a surgical material to protect wounds. However, the collagen based material is ineffective to stop oozing the body fluid and to hinder microorganisms from entering through it. Moreover, with the collagen-based material, epidermal cells are unable to regenerate where a third degree burn is caused or where a cut is made so deeply as no epidermis cell is left there.

Apart from those problems, a man-made skin needs to satisfy the following conditions. First of all, it must finally turn into part of the living skin after having a role in healing. A man-made skin has to promote the regeneration of dermis and epidermis from the surrounding normal tissue. A ideal man-made skin is required to have following properties.

1. It has to be able to control the amount of evaporating moisture at an optimal rate.
2. It has to be moistened enough to help proliferation of tissue cells and have a good affinity with regenerating tissue.
3. It must not produce a toxic substance at the time enzymes cause a decomposition reaction.
4. It has to be able to completely shut out microorganisms from outside.

SUMMARY OF THE INVENTION

Under the circumstances, the present inventors made an extensive study to eliminate the drawbacks of conventional collagen-based surrogate skins and have finally succeeded in accomplishing the present invention. That is, the present invention pertains to a double-layered man-made skin characterized by laminating a sheet of collagen sponge and a membrane of a poly-α-amino acid which has a good affinity with tissue cells and an appropriate permeability for moisture.

BRIEF DESCRIPTION OF THE DRAWINGS

FIG. 1 is a cross-sectional view of a man-made skin according to the present invention;

FIG. 2 is a schematic diagram showing a progress that a wound is on its way to healing up by the use of said man-made skin; where the numeral 1 designates a collagen sponge sheet, the numeral 2 designates a poly-α-amino acid membrane, the numeral 3 designates the normal epidermis, the numeral 4 designates the endothelium and the numeral 5 designates an interface into which the epidermis has penetrated keeping on proliferation.

DETAILED DESCRIPTION OF THE INVENTION

Copoly-α-amino acid prepared in the present work are composed of hydrophilic moiety and hydrophibic moiety, whose molecular weight is in the range of 100,000 to 200,000. These copolymer membranes have a good tissue compatibility and an appropriate permeability for moisture.

(1) Copoly(γ-benzyl-L-glutamyl-$N^5$-hydroxyalkyl-L-glutamine)

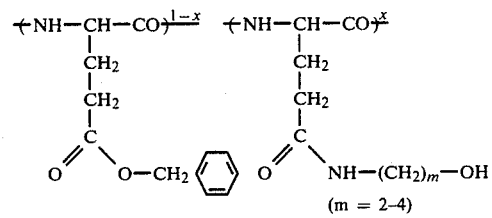

(m = 2-4)

(2) Copoly(γ-benzyl-L-glutamyl-$N^5$-dihydroxyethylaminopropyl-L-glutamine)

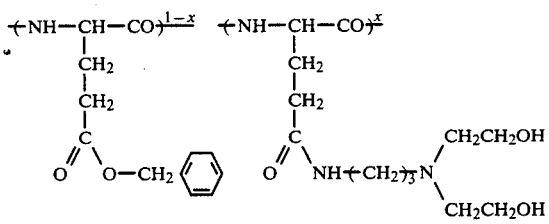

In the above formulae, x stands for a molar ratio of two glutamine derivatives contained in the copolymer.

Meanwhile, the γ-benzyl-L-glutamate group brings about a hydrophobicity and the $N^5$-hydroxyalkyl-L-glutamine group brings about a hydrophilicity. The present inventors have already published a process for synthesizing the copolymer in Journal of Polymer Science, Polymer Chemistry Edition, 21, 1289-1303 (1983). The synthesizing process is outlined by the following reaction equations.

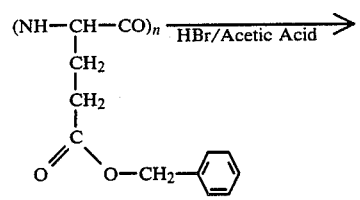

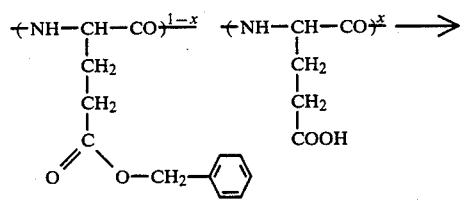

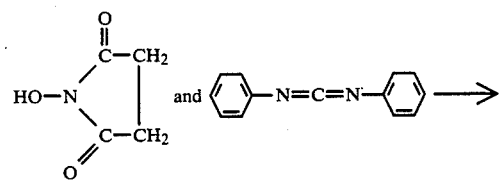

-continued

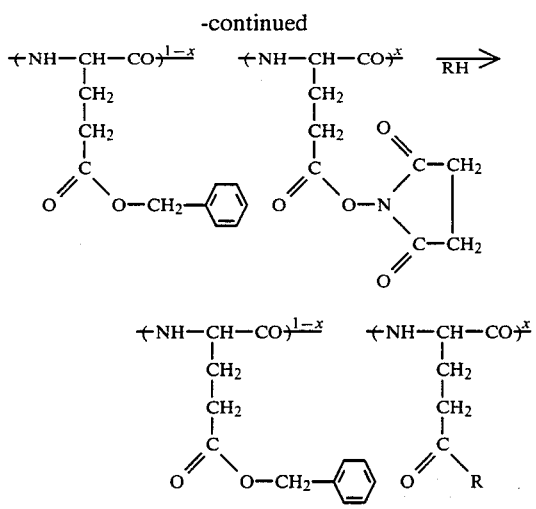

where R stands for

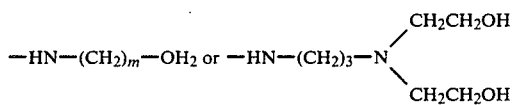

Low molecular weight substance are allowed to pass through the hydrated poly-α-amino acid membrane but microorganisms are blocked completely; therefore, the above conditions (1) and (4) can fully be satisfied. Moreover, fibroblasts were observed to proliferate normally on a poly-α-amino acid membrane having 20–40 percent of the hydrophilic amino acid residue, the condition (2) is also fully satisfied.

The poly-α-amino acid is slowly biodegradated into fragments inside a living body by a variety of peptidases, but when applied outside as a component of the man-made skin, it decomposes at an extremely slow rate because of scantiness of enzymes. From this reason, the decomposition rate is as small as negligible for about one or two months until a wound recovers. The lamination of a poly-α-amino acid membrane on a sheet of collagen sponge can merely be made with an organic solvent which can swell or dissolve both the components together in part.

Accordingly, the man-made skin of the present invention has a great advantage in the application to a living body; hence, it well satisfies the condition (3) at the same time. As apparent from the above, the poly-α-amino acid membrane of this invention satisfies all the conditions (1) to (4) required for a man-made skin at a time, which is able to be accomplished by the lamination of the poly-α-amino acid membrane and the collagen sponge sheet.

EXAMPLE

A collagen solution is stirred vigorously by a homogenizer being kept below 20° C. so as to form a cream-like viscous solution. A collagen sponge sheet (1) which constitutes an essential part of the man-made skin of this invention is prepared from the solution by lyophilization. The apparent density of the collagen sponge sheet is in the range 0.01 to 0.05 g/cm³; it is desirable to be in the range 0.02 0.03 g/cm³. The mean diameter of pores left in the sheet ranges from 20 to 200 μm; it is preferable to be in the range of 30 to 100 μm. The thickness of the membrane can be changed at will so as to match for the depth of a wound; however, it commonly ranges from about 0.2 to about 0.3 mm.

It is desirable for a collagen sponge sheet to be cross-linked in advance by the use of an appropriate agent since the collagen sponge sheet becomes less soluble by cross-linking upon being kept standing in contact with a wound. Glutaraldehyde, hexamethylene diisocyanate and the like can be enumerated as a cross-linking agent. But hexamethylene diisocyanate is most preferable of all.

A poly-α-amino acid membrane (2) is prepared from a dimethyl formamide solution containing copoly(γ-benzyl-L-glutamyl-N⁵-hydroxypropyl-L-glutamine) by the casting method.

Subsequently, the collagen sponge sheet (1) and the copolymer membrane (2) are stuck together by virtue of an organic solvent which is able to swell or dissolve both the components together in part. FIG. 2 illustrates a condition in the progress of treatment in which a man-made skin thus obtained is applied on a wound where none of epidermis cells is found.

The collagen sponge sheet and the poly-α-amino acid membrane both satisfy the conditions that they can prevent the leakage of the body fluid and the infection due to microorganisms from outside; in addition, they can keep an appropriate permeability for moisture, which is very essential for a man-made skin.

Thanks to those properties, the collagen sponge sheet is able to stay moist to such an extent that fibroblasts are able to proliferate three-dimensionally. What is more, because the poly-α-amino acid is excellent in the affinity with tissue cells, it helps the surrounding normal epidermis grow and penetrate the interface (5) between the poly-α-amino acid membrane and a layer of fibroblasts growing inwardly in the collagen sponge. Like this, both the components work in association as an ideal man-made skin. When the surface of a wound is covered with the epidermis completely, the poly-α-amino acid membrane falls off by itself; in contrast with this, the collagen sponge sheet is gradually assimilated in the surrounding tissues after having played a general role of the dermis in the course of healing.

What is claimed is:

1. A man-made skin composed of two layers: collagen and a poly-α-amino acid, which is characterized by comprising sticking on a membrane of collagen sponge a membrane of a poly-α-amino acid which has a good affinity with tissue cells and an appropriate permeability for moisture.

2. A man-made skin as set forth in claim 1, in which said poly-α-amino acid is a copolymer which has a hydrophilic moiety and a hydrophobic moiety together.

3. A man-made skin as set forth in claim 2 in which the poly-α-amino acid is a copoly-(γ-benzyl-L-glutamyl-N⁵-hydroxyalkyl-L-glutamine) of the formula

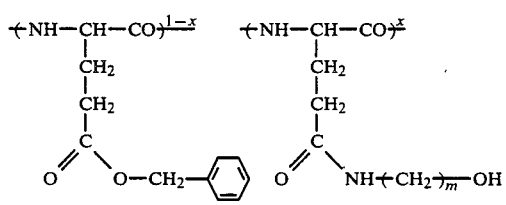

where
m=2 to 4 and x represents the molar ratios of the glutamine α-amino acids.

4. A man-made skin as set forth in claim 2 in which the poly-α-amino acid is a copoly(γ-benzyl-L-glutamyl-N⁵-dihydroxyethylaminopropyl-L-glutamine) of the formula

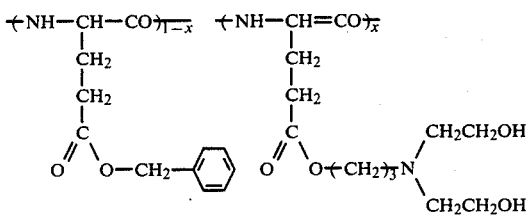

where x represents the molar ratios of the glutamine α-amino acids.

5. The man-made skin as set forth in claim 2 wherein the poly-α-amino acid copolymer has a molecular weight in the range of from abotu 100,000 to about 200,000.

6. A composite two-layer membrane suitable as an artificial skin for the promotion of healing of burns, cuts or wounds, which comprises
   a collagen sponge base layer to be used in contact with the exposed endothelium at the site of the burn, cut or wound, said collagen sponge having an apparent density of from 0.01 to 0.05 g/cm³, a thickness in the range of from about 0.2 to about 0.3 mm, and a pore structure such that the mean diameter of the pores is in the range of from about 20 to 200 μm; and
   a membrane of a moisture permeable poly-α-amino acid laminated to one surface of the collagen sponge base layer, said poly-α-amino acid being a copolymer of a first α-amino acid having a hydrophilic moiety with a second α-amino acid having a hydrophobic moiety,
   whereby said composite two-layer membrane promotes three-dimensional proliferation of fibroblasts and the normal epidermal cells surrounding the burn, cut or wound can grow and penetrate the interface between the collagen sponge base layer and the poly-α-amino acid membrane.

7. The composite membrane of claim 6 wherein the collagen sponge is cross-linked.

8. The composite membrane of claim 6 wherein the collagen sponge has an apparent density of from 0.02 to 0.03 g/cm³ and a mean pore diameter in the range of 30 to 100 μm.

9. The composite membrane of claim 7 wherein the poly-α-amino acid copolymer has the formula

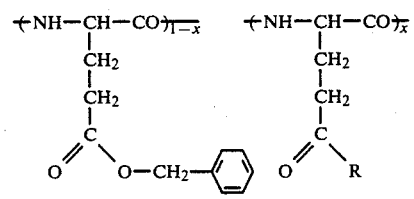

where R is

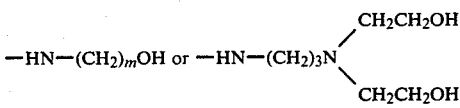

where
   m is 2 to 4, and
   x represents the molar ratios of the glutamine amino acids.

* * * * *

UNITED STATES PATENT AND TRADEMARK OFFICE
CERTIFICATE OF CORRECTION

PATENT NO. : 4,642,118
DATED : Feb. 10, 1987
INVENTOR(S) : TOSHIMITSU KUROYANAGI, ET AL.

It is certified that error appears in the above-identified patent and that said Letters Patent is hereby corrected as shown below:

ON THE TITLE PAGE

[30] Foreign Application Priority Data

Delete "Nov. 6, 1984",
Insert --June 11, 1984--.

Signed and Sealed this

Twenty-ninth Day of September, 1987

Attest:

DONALD J. QUIGG

*Attesting Officer*   *Commissioner of Patents and Trademarks*